United States Patent [19]

Gotanda et al.

[11] Patent Number: 4,987,314
[45] Date of Patent: Jan. 22, 1991

[54] ACTUATOR APPARATUS UTILIZING A SHAPE-MEMORY ALLOY

[75] Inventors: Masakazu Gotanda, Kanagawa; Yasuhiro Ueda, Kokubunji, both of Japan

[73] Assignee: Olympus Optical Co., Ltd., Tokyo, Japan

[21] Appl. No.: 522,464

[22] Filed: May 11, 1990

Related U.S. Application Data

[63] Continuation of Ser. No. 464,630, Jan. 3, 1990, abandoned, which is a continuation of Ser. No. 308,808, Feb. 9, 1989, abandoned.

[30] Foreign Application Priority Data

Apr. 21, 1988 [JP] Japan .................................. 63-99043
May 30, 1988 [JP] Japan ............................. 63-70291[U]

[51] Int. Cl.$^5$ ............................................. G02B 27/00
[52] U.S. Cl. ...................................... 250/551; 337/140
[58] Field of Search ................... 250/551, 215, 227.11; 337/140; 307/99

[56] References Cited

U.S. PATENT DOCUMENTS

| | | | |
|---|---|---|---|
| 4,495,421 | 1/1985 | Endo et al. | 250/551 |
| 4,520,336 | 5/1985 | Hastings et al. | 337/140 |
| 4,601,283 | 7/1986 | Chikama | 128/4 |
| 4,799,474 | 1/1989 | Ueda | 128/4 |

FOREIGN PATENT DOCUMENTS

| | | |
|---|---|---|
| 61-94631 | 5/1986 | Japan . |
| 62-26041 | 2/1987 | Japan . |
| 63-21065 | 1/1988 | Japan . |
| 63-21066 | 1/1988 | Japan . |

Primary Examiner—David C. Nelms
Attorney, Agent, or Firm—Frishauf, Holtz, Goodman & Woodward

[57] ABSTRACT

An actuator apparatus includes a plurality of actuators each having a shape-memory alloy, a power supply line unit for supplying power to the actuators, power supply control unit connected in series with at least one of the actuators, and a driving unit for driving the power supply control unit.

25 Claims, 4 Drawing Sheets

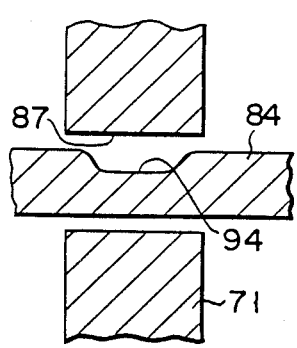
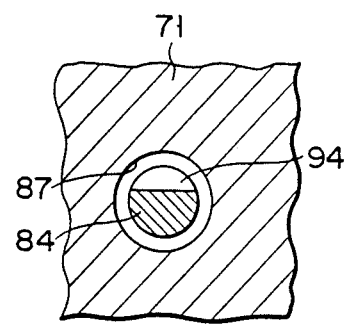
FIG. 7
FIG. 8
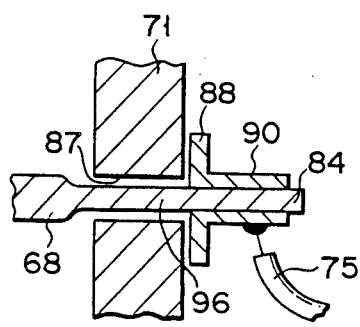
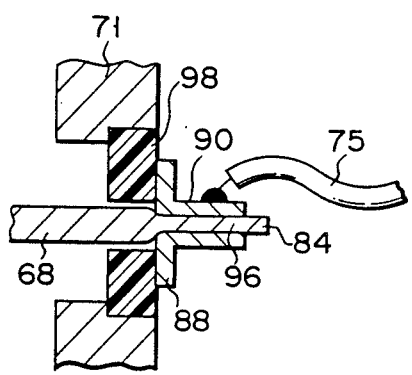
FIG. 9
FIG. 10

4,987,314

ACTUATOR APPARATUS UTILIZING A SHAPE-MEMORY ALLOY

This application is a continuation, of application Ser. No. 07/464,630, filed Jan. 3, 1990, now abandoned which in turn is a continuation of Ser. No. 07/308,808, filed Feb. 9, 1989, now abandoned.

BACKGROUND OF THE INVENTION

1. Field of the Invention

The present invention relates to an actuator apparatus utilizing a shape-memory alloy.

2. Description of the Related Art

In recent years, actuators using shape-memory alloys have been provided. An example of these actuators is a cable having a bending mechanism disclosed in Japanese Utility Model Disclosure (Kokai) No. 61-94001. In this apparatus, a plurality of actuators having shape-memory alloys are placed in a cable, and the actuators are independently energized to bend the cable.

That is, power supply lines are independently connected to the actuators including a shape-memory alloy, and an actuator to be activated is energized via the independent power supply line or the supplied power is changed for each actuator, thereby controlling operations of the actuators.

In this conventional actuator apparatus, however, the independent power supply line is connected to each shape-memory alloy constituting the actuator. Therefore, the number of power supply lines is increased in proportion to the number of actuators or shape-memory alloys. That is, since each shape-memory alloy requires two power supply lines, the total number of power supply lines required becomes twice that of shape-memory alloys.

Since an electrical resistance of a shape-memory alloy is generally low, a higher current value is required for heating the shape-memory alloy. For this reason, a power supply line must have a relatively high current capacity. Therefore, a large-diameter wire material is used for a power supply line.

Wiring using a large number of electrical wires having a large diameter is very problematic in realizing a compact and light actuator. In addition, a large-diameter electrical wire is undesirable if an actuator is applied to a cable apparatus or an endoscope which is long in shape because the length of a power supply line is also increased. Also, when a power supply time is prolonged or power supply is repeatedly performed, heat generated from power supply lines may be accumulated to lead to overheating.

SUMMARY OF THE INVENTION

It is, therefore, an object of the present invention to make an actuator apparatus utilizing a shape-memory alloy compact and light in weight, and to improve its safety.

The above object of the present invention is achieved by the following actuator apparatus. That is, this actuator apparatus comprises: a plurality of actuators each having a shape-memory alloy; power supply line means for supplying power to the actuators; power supply control means connected in series with at least one of the actuators; and driving means for driving the power supply control means.

In the actuator apparatus according to the present invention, a power supply line for supplying power from a power source to each actuator need not be provided to each actuator but can be commonly used by a plurality of actuators. Therefore, the actuator can be made compact and light in weight.

In addition, since the number of power supply lines can be decreased, heat generated by the power supply lines can be reduced, and the safety of the actuator can be improved.

BRIEF DESCRIPTION OF THE DRAWINGS

FIGS. 7 and 8 are longitudinal and cross sectional views showing a portion encircled in FIG. 6;

FIG. 9 is a sectional view showing an actuator mounting portion according to a first modification of the second embodiment;

FIG. 10 is a sectional view showing an actuator mounting portion according to a second modification;

DETAILED DESCRIPTION OF THE PREFERRED EMBODIMENTS

Embodiments of the present invention will be described in detail below with reference to the accompanying drawings.

Figure 1:
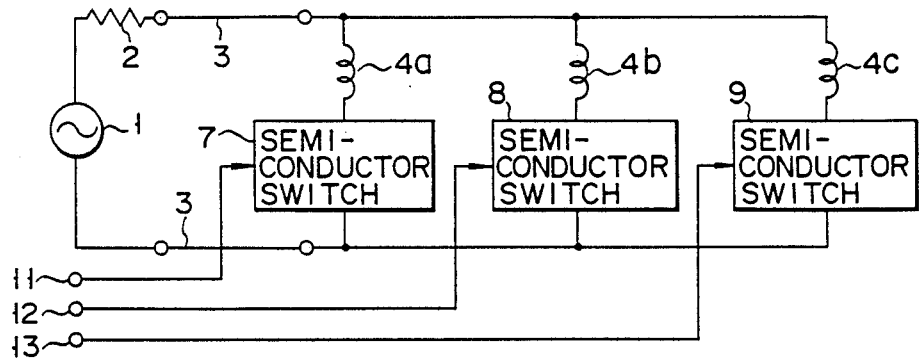
FIG. 1 is a block diagram showing an actuator apparatus according to a first embodiment of the present invention.

FIG. 1 shows a first embodiment of the present invention. A power source 1 is connected to a pair of power supply lines or paths 3 via an overheat preventing resistor 2. A plurality of actuators 4a, 4b and 4c are connected in parallel with the power supply lines 3. Each of the actuators 4a, 4b and 4c has a shape-memory alloy and deforms with self-generated heat upon power supply. Power supply control means are connected in series with the actuators 4a, 4b and 4c, respectively. The power supply control means are, e.g., semiconductor switches 7, 8 and 9. By supplying power supply signals to power supply control terminals 11, 12 and 13 connected to the semiconductor switches, the semiconductor switches are turned on.

In order to supply power to and drive any of the actuators 4a, 4b and 4c, the power supply signal is supplied to a corresponding one of the terminals 11, 12 and 13, thereby turning on a corresponding one of the semiconductor switches 7, 8 and 9. As a result, the selected one of the actuators 4a, 4b and 4c is powered and deforms with self-generated heat.

In order to flow a current required for allowing the actuators 4a, 4b and 4c to generate heat, each of the power supply lines or paths 3 must be a cable having a relatively high power supply capacity, i.e., a relatively thick cable. Only a small current, however, is required for the power supply signal to be supplied to the terminals 11, 12 and 13 in order to turn on the switches 7, 8 and 9. Therefore, a very thin cable can used as a transmission line for transmitting the power supply signal.

For example, in order to connect the power supply line 3 for power supply and heating to each of the actuators 4a, 4b and 4c, six power supply cables are required. In addition, each power supply cable must be a relatively high power supply capacity, i.e., a relatively thick cable.

The present invention, however, requires only two power supply lines 3 having a high power supply capacity and three very thin cables for transmitting the power supply signals to the semiconductor switches 7, 8 and 9. As a result, a power supply circuit can be made compact and light in weight.

Especially when the actuators 4a, 4b and 4c are separated from the power source 1, compact and light power supply cables and signal lines are very advantageous.

Also, the overheat preventing resistor 2 prevents overheating of the actuators 4a, 4b and 4c caused by flow of an excessive current to the lines 3. In the present invention, only one resistor 2 is necessary because the number of power supply lines 3 is two.

Figure 2:
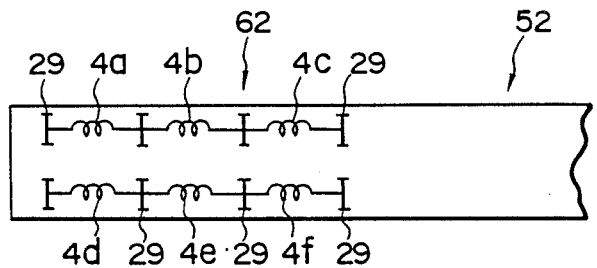
FIG. 2 is a schematic view showing an actuator according to a first modification of the first embodiment.
Figure 3:
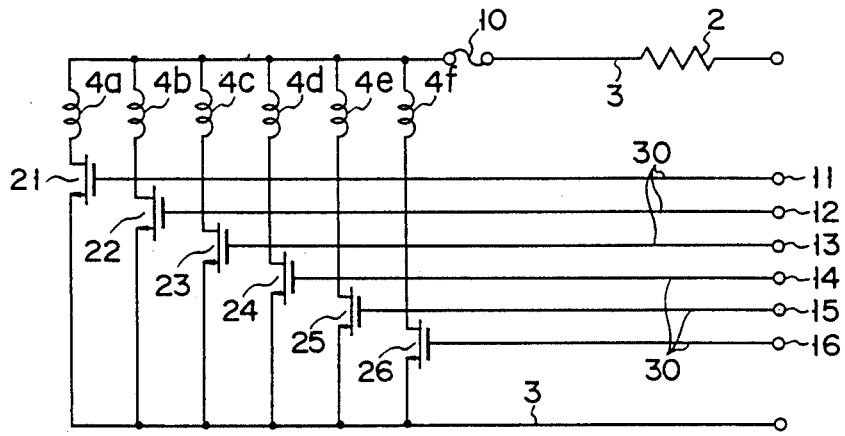
FIG. 3 is a circuit diagram showing the actuator apparatus according to the first modification.

FIGS. 2 and 3 show a first modification of the actuator according to the first embodiment. In this modification, MOS field effect transistors 21 to 26 are used as semiconductor switches of power supply control means, and a current flowing through a drain-source path of each of the transistors 21 to 26 is controlled by a voltage applied to the gate of each transistor. The voltage is applied to the gate of each transistor via a corresponding one of power supply control terminals 11 to 16 connected to the transistors 21 to 26, respectively. Any of the transistors 21 to 26, to the gate of which the voltage is applied, is turned on. In this manner, a selected one of actuators 4a to 4f is powered and deforms by self-generated heat.

Each of the actuators 4a to 4f is formed like a coil spring and is arranged in a flexible portion 62 of an insertion portion 52 of an endoscope, as shown in FIG. 2. Pairs of three actuators 4a, 4b and 4c, and 4d, 4e and 4f are aligned in series with each other at upper and lower portions along the axial direction of the flexible portion 62, respectively. The respective actuators are connected via fixing members 29. The transistors 21 to 26 for controlling power supply to the actuators 4a to 4f are arranged near these actuators 4a to 4f, respectively. Power supply lines 3 and signal lines 30 for supplying power supply signals to the transistors 21 to 26 extend to a manipulation portion (not shown) through inside the insertion portion 52 of the endoscope. A temperature fuse 10 is inserted midway along the line 3.

This actuator apparatus is incorporated in the endoscope such that the actuators 4a to 4f are separated from a driving power source 1 by a very long distance. In the present invention, however, the number of power supply lines 3 having a high power supply capacity is only two. In addition, each signal line 30 for supplying the power supply signal to a corresponding one of the transistors 21 to 26 can be a very thin wire. Therefore, the insertion portion 52 of the endoscope can be rendered very thin.

In the first modification, since the MOSFETs 21 to 26 are used as the power supply control means, a required gate voltage is low, and therefore a very thin signal line 30 can be used to apply a voltage to the gate. In addition, the number of actuators can be easily increased because the number of power supply lines need not be increased.

Figure 4:
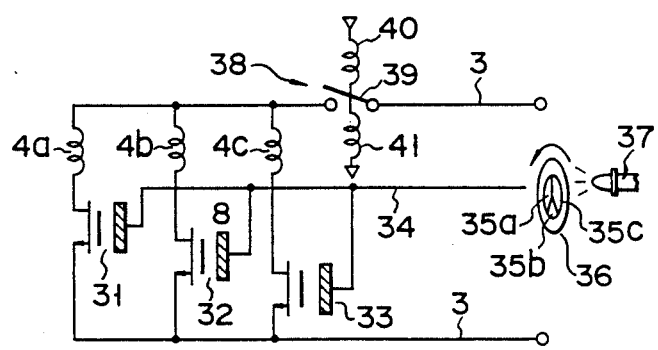
FIG. 4 is a circuit diagram showing an actuator apparatus according to a second modification of the first embodiment.

FIG. 4 shows a second modification. In this modification, phototransistors 31 to 33 are used as semiconductor switches of power supply control means, and an element responsive to specific light incident through an optical fiber 34 is used as each of the phototransistors 31 to 33. Therefore, the drain-source path of each phototransistor is conducted upon incidence of the specific light. As a result, a selected one of actuators 4a to 4f is powered and deforms by self-generated heat.

A filter rotary unit 36 comprising a plurality of filters 35a to 35c having different spectral characteristics is located at the incident end of the fiber 34. A light source 37 is located before the rotary unit 36 to oppose the incident end of the fiber 34.

In order to activate the actuator apparatus, the rotary unit 36 is rotated to select one of the filters, the light from the light source 37 is separated through the filter opposing the incident end of the fiber 34, and the separated light is guided to become incident on the fiber 34. As a result, although the incident light reaches all the phototransistors 31 to 33 through the fiber 34, only a phototransistor having the characteristics matching the light is turned on, and a corresponding actuator generates heat and deforms.

In the second modification, a normally-closed switch 38 is inserted midway along a power supply line 3. A movable contact 39 of the switch 38 is connected to an overheat preventing coil 40 having a shape-memory alloy. The contact 39 is also connected to a bias spring 41 for normally applying a bias against the coil 40. The coil 40 is located near the actuators 4a to 4c and deforms to open the contact 39 when the actuators 4a to 4c generate heat, thereby interrupting power supply to the actuators.

In the first embodiment of the present invention, a multiplexer circuit may be used as the power supply control means.

A second embodiment of the actuator apparatus according to the present invention will next be described below.

Figure 5:
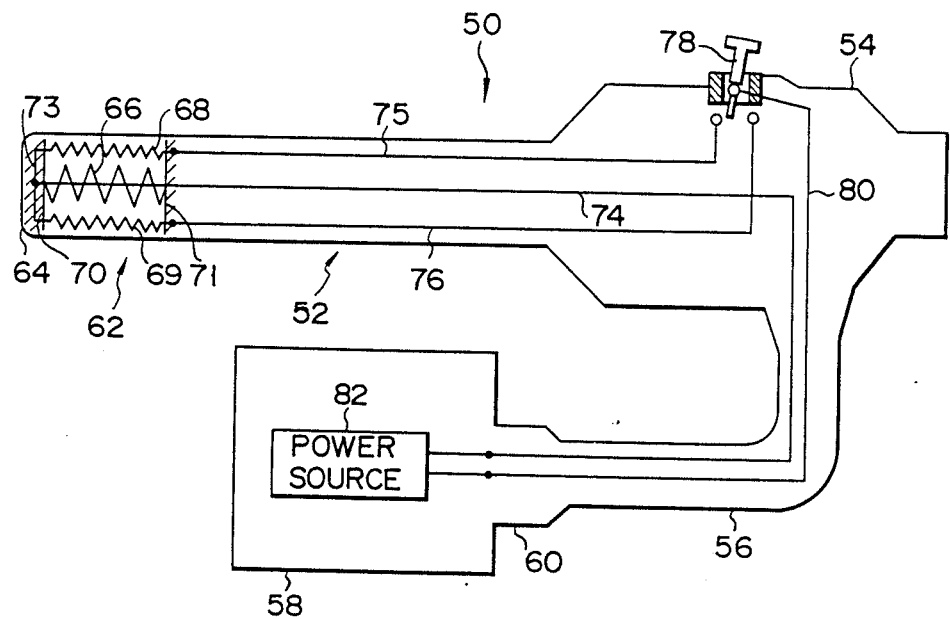
FIG. 5 is a schematic view showing an endoscope in which the actuator apparatus according to a second embodiment is mounted.

FIGS. 5 to 8 show the second embodiment of the present invention. Referring to FIG. 5, an endoscope 50 comprises an insertion portion 52, a manipulation portion 54 and a universal cord 56. A connector 60 is connected to the distal end of the cord 56 so as to be freely attached/detached with respect to a light source unit 58.

A bending portion 62 is formed in the insertion portion 52 of the endoscope 50. The bending portion 62 can be bent to change the direction of a distal end portion 64 of the insertion portion 52. That is, a coil spring 66 is located at the center of the bending portion 62, and driving coil members 68 and 69 having a shape-memory alloy are located at upper and lower positions of the spring 66. The distal and proximal ends of each of the spring 66 and the coil members 68 and 69 are connected to support plates 70 and 71, respectively. The shape-memory alloy constituting the coil members 68 and 69 is a coil-like Ni-Ti-based alloy, Cu-Zn-Al-based alloy or the like. The coil is caused to memorize a dense coil shape and extended and fixed to the plates 70 and 71, as shown in FIG. 5. A transformation temperature Af of the shape-memory alloy used as the coil members 68 and 69 is set to be, e.g., 30° to 60° C.

The distal ends of the coil member 68 and 69 are connected via a common lead 73 which is connected to another lead 74. The other ends of the coil members 68 and 69 are connected to leads 75 and 76, respectively. The leads 75 and 76 are connected through the insertion portion 52 to a stationary terminal of a bend manipulating switch 78 located in the manipulation portion 54 and comprising a bidirectional contact. A switching movable contact of the switch 78 is connected to another lead 80. The leads 80 and 74 are connected to a power source 82 located in the light source unit 58 through the universal cord 56.

In the second embodiment, since the driving coil members 68 and 69 are identical, only the coil member 68 will be described below.

Figure 6:
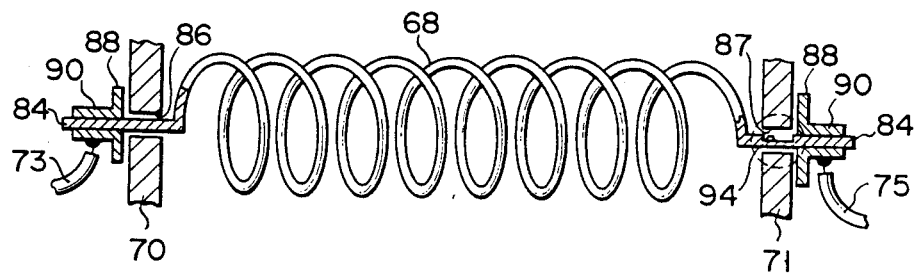
FIG. 6 is a partial sectional view showing the actuator according to the second embodiment.

FIG. 6 shows a structure of the coil member 68. End portions 84 of the coil member 68 are linearly formed and inserted in mounting holes 86 and 87 formed in the plates 70 and 71, respectively. A fixing member 90 with a flange 88 is fixed to an insertion portion of each end portion 84 by mechanical caulking. The flanges 88 of the fixing members 90 abut against the plates 70 and 71 to support the tension of the coil member 68 when the member 68 is heated. The leads 73, 75 and 76 are soldered to the fixing members 90.

As shown in FIGS. 7 and 8, a notch 94 is formed in a middle portion of one linear end portion 84 of the coil member 68, thereby reducing the sectional area of the middle portion. Therefore, this middle portion having the notch 94 breaks most easily in the coil member 68. For this reason, the middle portion breaks when excessive power supply heating is performed to the coil member 68, thereby releasing a driving force of the member 68.

An operation of the endoscope 50 having the above arrangement will be described below. In order to bend the bending portion 62 of the insertion portion 52, the bend manipulating switch 78 is switched from a neutral position toward a position which enables bending. For example, when the switch is set backward, the lead 75 connected to the upper driving coil member 68 and the lead 80 are conducted to supply power to the upper coil member 68. The coil member 68 generates heat by its own resistance and is heated up to the transformation temperature Af or more. As a result, the coil member 68 is apt to recover the dense coil form as its initial memory shape and therefore bends the bending portion 62 by this recovering force.

If the above operation is normally performed, no problem arises. If an excessive current is flowed through the coil member 68 for a certain reason, however, the coil member 68 is overheated, and the temperature at the middle portion of the end portion 84 having a higher resistance because the notch 94 is formed becomes higher to break the middle portion. As a result, the driving force of the coil member 68 is released to no longer bend the bending portion 62, and the bending portion 62 recovers its original form.

FIG. 9 shows a first modification of the second embodiment. In this second embodiment, since both end portions of the driving coil member are similarly arranged, a structure of only one end portion will be described below.

In this modification, no notch 94 is formed in a middle portion of an end portion 84 of a driving coil member 68, and a small-diameter portion 96 is formed throughout the entire length of one end portion 84. The small-diameter portion 96 is inserted in a mounting hole 87 formed in a support plate 71, and a fixing member 90 with a flange 88 is fixed to the inserted distal end portion by mechanical caulking. The flange 88 of the fixing member 90 abuts against the plate 71 and supports the tension of the coil member 68 when the member 68 is heated. A lead 75 is soldered to the fixing member 90. The other arrangement of is similar to the second embodiment.

Also in this modification, therefore, the small-diameter portion 96 of the coil member 68 is easiest to break mechanically and generates the largest amount of heat by its own resistance when the coil member 68 is powered. Although no problem is posed as long as the operation is normally performed, therefore, if an excessive voltage or current is applied to the coil member 68 for a certain reason, the temperature at the small-diameter portion having the smallest cross sectional area, i.e., the highest resistance becomes higher to break the portion 96. As a result, the driving force of the coil member 68 is released to stop bending, thereby releasing the bent state.

FIG. 10 shows a second modification of the second embodiment. In this modification, as in the first embodiment, a small-diameter portion 96 is formed throughout the entire length of an end portion 84 of a driving coil member 68, and a fixing member 90 with a flange 88 is fixed to the small-diameter portion 96 by mechanical caulking. The fixing member 90, however, is supported by a support plate 71 via a fixing ring 98 having a heat-melting material. The heat-melting material for forming the ring 98 may be arbitrarily selected from a polyurethane resin, a vinyl chloride resin and the like.

Also in the second modification, therefore, the small-diameter portion 96 of the coil member 68 is easiest to break mechanically. In addition, when overheating occurs, the ring 98 having the heat-melting material melts and is removed from the plate 71. As a result, the driving force of the coil member 68 is released to stop bending, thereby releasing the bent state.

Figure 11:
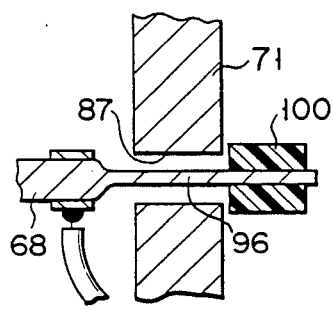
FIGS. 11 and 12 are sectional views showing an actuator mounting portion according to a third modification.
Figure 12:
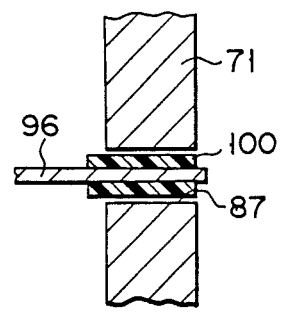

FIGS. 11 and 12 show a third embodiment of the present invention. In this modification, a heat-shrinkable tube 100 is fitted on a small-diameter portion 96 of a driving coil member 68 by an adhesion or the like. The tube 100 abuts against and is supported by a support plate 71 when the coil member 68 is heated. When the tube 100 shrinks by heat, it can be inserted in a mounting hole 86 of the plate 71 and the coil member 68 is removed.

Also in the third embodiment, therefore, if an excessive power is supplied to the coil member 68 to cause overheating, the tube 100 shrinks by the heat and is removed from the plate 71 as shown in FIG. 12. As a result, the driving force of the coil member 68 is released to stop bending, thereby releasing the bent state.

Figure 13:
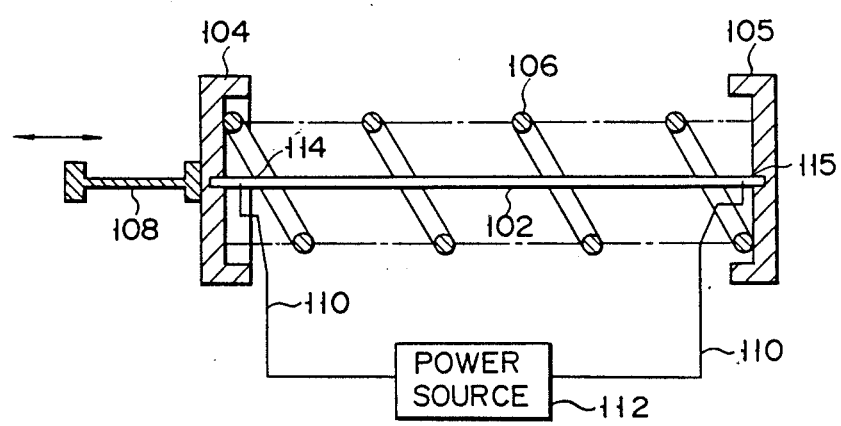
FIG. 13 is a longitudinal sectional view according to a fourth modification.
Figure 14:
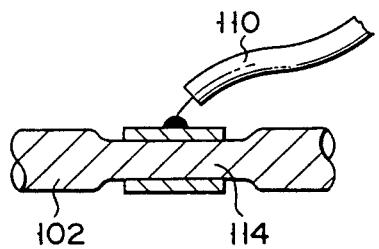
FIG. 14 is a sectional view showing an actuator end portion shown in FIG. 13.

FIGS. 13 and 14 show a fourth modification. In this modification, an actuator apparatus is arranged to shrink along the axial direction. That is, both ends of a wire 102 having a shape-memory alloy are fixed to mounting members 104 and 105, and a bias coil spring 106 is inserted between the mounting members 104 and 105. A rod 108 is fixed to the mounting member 104. Leads 110 are connected to both ends of wire 102 having a shape-memory alloy. The other ends of the leads 110 are connected to a power supply source 112.

As shown in FIGS. 13 and 14, small-diameter portions 114 and 115 are formed at two end portions of the shape-memory-alloy wire 102 and soldered to the lead 110, respectively.

In this actuator apparatus, the coil spring 106 applies a biasing force to the mounting members 104 and 105 so that the wire 102 is kept extended.

When the wire 102 having a shape-memory alloy is powered by the power source 112 through the leads 110, the wire 102 is apt to return to its original (memory) length. When power supply is stopped, the wire 102 recovers its initial state. By repeating this operation, the rod 108 can reciprocate along the axial direction.

When the above operation is normally performed, no problem arises. If an excessive voltage or current is applied to the wire 102, however, the wire 102 is overheated. As a result, the temperature at the small-diameter portions 114 and 115 having a higher resistance becomes higher to break these portions. Therefore, the driving force of the wire 102 is released to assure the safety of the apparatus.

In the actuator apparatus according to the second embodiment of the present invention, the means for releasing the driving force of the driving member if excessive power supply heating is performed is provided to the driving member having a shape-memory alloy. Therefore, the safety of the actuator can be assured.

What is claimed is:

1. An actuator apparatus comprising:
   a plurality of actuators each comprising a shape-memory alloy;
   power supply line means for supplying power to said actuators;
   power supply control means connected in series with at least one of said actuators; and
   driving means for driving said power supply control means.

2. The apparatus according to claim 1, wherein said power supply control means includes a semiconductor switch.

3. The apparatus according to claim 2, wherein said semiconductor switch includes a MOS field effect transistor.

4. The apparatus according to claim 2, wherein said semiconductor switch includes a phototransistor.

5. The apparatus according to claim 4, wherein said driving means includes an optical fiber for guiding light to said phototransistor, and a light source and an optical filter for supplying light to said optical fiber.

6. The apparatus according to claim 1, further comprising:
   a holding member for holding said actuators; and
   disabling means for disabling an operation of said actuators when said actuators are overheated.

7. The apparatus according to claim 6, wherein said disabling means for disabling an operation of said actuators includes separating means for separating said actuators from said holding member.

8. The apparatus according to claim 7, wherein said actuator separating means includes a small-diameter portion formed at an end portion of said shape-memory alloy.

9. The apparatus according to claim 7, wherein said actuator separating means includes a heat-melting member located at an end portion of said shape-memory alloy.

10. The apparatus according to claim 7, wherein said actuator separating means includes a heat-shrinkable member located at an end portion of said shape-memory alloy.

11. The apparatus according to claim 1, wherein:
    said power supply line means includes a pair of power supply lines; and
    said plurality of actuators are connected in parallel to said power supply lines; and
    said plurality of actuators are connected in parallel to said supply lines.

12. The apparatus according to claim 11, wherein:
    said power supply control means includes semiconductor switches; and
    each semiconductor switch is connected in series with each actuator.

13. The apparatus according to claim 12, wherein said actuators are arranged in an insertion section of an endoscope.

14. The apparatus according to claim 13, wherein said semiconductor switches are arranged in the insertion section of the endoscope.

15. An actuator apparatus comprising:
    a plurality of actuators each comprising a shape-memory alloy;
    power supply line means for supplying power to said actuators;
    power supply control means connected in series with at least one of said actuators; and
    driving means for driving said power supply control means;
    said power supply line means including a pair of power supply lines, and said plurality of actuators being connected in parallel to said power supply lines.

16. The apparatus according to claim 15, wherein said power supply control means includes switch means connected in series with each of said actuators.

17. The apparatus according to claim 16, wherein said actuators are arranged in an insertion section of an endoscope.

18. The apparatus according to claim 17, wherein at least one of said power supply lines extends into the insertion section of the endoscope.

19. The apparatus according to claim 18, wherein said switch means is arranged in the insertion section of the endoscope.

20. The apparatus according to claim 19, wherein said switch means includes a semiconductor switch.

21. An actuator apparatus comprising:
    a plurality of actuators each comprising a shape-memory alloy;
    power supply line means for supplying power to said actuators;
    power supply control means connected in series with at least one of said actuators; and
    driving means for driving said power supply control means;
    said actuators and said power supply control means being arranged in an insertion section of an endoscope.

22. The apparatus according to claim 21, wherein:
    said power supply line means includes a pair of power supply lines; and
    said plurality of actuators are connected in parallel to said power supply lines.

23. The apparatus according to claim 22, wherein at least one of said power supply lines extends into the insertion section of the endoscope.

24. The apparatus according to claim 23, wherein said power supply control means includes switch means connected in series with each of said actuators.

25. The apparatus according to claim 24, wherein said switch means includes a semiconductor switch.

* * * * *